United States Patent [19]

Sauer et al.

[11] Patent Number: 4,851,571

[45] Date of Patent: Jul. 25, 1989

[54] PROCESS FOR THE PRODUCTION OF ISOCYANATES

[75] Inventors: Heinz Sauer; Hermann Dallmeyer, both of Odenthal; Uwe J. Zarnack, Brunsbuettel; Berthold Keggenhoff; Bernd Weber, both of Krefeld, all of Fed. Rep. of Germany

[73] Assignee: Bayer Aktiengesellschaft, Bayerwerk, Fed. Rep. of Germany

[21] Appl. No.: 190,555

[22] Filed: May 5, 1988

[30] Foreign Application Priority Data

May 21, 1987 [DE] Fed. Rep. of Germany ....... 3717057

[51] Int. Cl.$^4$ .......................................... C07C 118/00
[52] U.S. Cl. .................................................... 560/347
[58] Field of Search .......................................... 560/347

[56] References Cited

U.S. PATENT DOCUMENTS

| | | | |
|---|---|---|---|
| 3,251,577 | 5/1966 | Bolanowski et al. | 259/7 |
| 3,321,283 | 5/1967 | Ewald | 23/283 |
| 3,947,484 | 3/1976 | Mitrowsky et al. | 260/453 |
| 4,289,732 | 9/1981 | Bauer et al. | 422/224 |
| 4,419,295 | 12/1983 | Hennig et al. | 260/453 |

FOREIGN PATENT DOCUMENTS 1238669 7/1971 United Kingdom .

*Primary Examiner*—Alan Siegel
*Attorney, Agent, or Firm*—Gene Harsh; Joseph C. Gil; Thomas W. Roy

[57] ABSTRACT

The present invention is directed to a process for the production of a mono- and/or polyisocyanate by the phosgenation of a mono- and/or polyamine in a mixer which comprises (a) a casing having at least two inlets and at least one outlet,
(b) a rotatable shaft extending through the casing,
(c) at least one rotor disc attached to the shaft such that the rotor disc is perpendicular to the shaft,
(d) at least one stator disc attached to the casing such that the stator disc is parallel to the rotor disc and has an opening such that the shaft can pass through the stator disc,
(e) optionally at least one running wheel attached to the shaft and containing openings such that when the shaft is rotating the running wheel provides a pumping effect to the reaction mixture passing through the mixer,
(f) at least one inlet through the casing for introducing a phosgene solution axially to the shaft and against the rotor disc,
(g) at least one inlet through the casing for introducing a mono- and/or polyamine amine solution or suspension against the rotor disc at a point which is radially outward from inlet (f), by introducing the phosgene solution and the amine solution or suspension through inlets (f) and (g) while rotating the shaft, further reacting the reaction mixture at an elevated temperature downstream of the mixer and finally purifying the resultant isocyanate to form the mono- or polyisocyante.

8 Claims, 1 Drawing Sheet

PROCESS FOR THE PRODUCTION OF ISOCYANATES

BACKGROUND OF THE INVENTION

1. Field of the Invention

The present invention is directed to a process for the production of polyisocyanates by the phosgenation of polyamines using a special mixer.

2. Description of the Prior Art

In chemical technology, polyisocyanates are primarily produced by the conversion of primary amines with phosgene, wherein both reaction components are customarily dissolved or suspended in a suitable solvent.

The efficiency of mixing these reaction components considerably influences the degree of purity of the product. The purity also depends on the kind of mixer and whether the product is formed without clumps or caking.

Special nozzle arrangements have been used for this purpose (DE-PS No. 1,792,660 corresponding to GB-PS No. 1,238,669; DE-OS No. 2,950,216 corresponding to U.S. Pat. No. 4,289,732: EP-OS No. 65,727 corresponding to U.S. Pat. No. 4,419,295) as well as pumps such as centrifugal pumps (DE-PS No. 2,153,268 corresponding to U.S. Pat. No. 3,947,484). In spite of all efforts, the formation of clumps and blockages cannot be avoided during mixing of the two components.

Accordingly, it is an object of the present invention to be able to prepare polyisocyanates by the phosgenation of polyamines without the formation of clumps or cakes. This object may be achieved in accordance with the process of the present invention as set forth hereinafter.

SUMMARY OF THE INVENTION

The present invention is directed to a process for the production of a mono- and/or polyisocyanate by the phosgenation of a mono- and/or polyamine in a mixer which comprises
  (a) a casing having at least two inlets and at least one outlet,
  (b) a rotatable shaft extending through the casing,
  (c) at least one rotor disc attached to the shaft such that the rotor disc is perpendicular to the shaft,
  (d) at least one stator disc attached to the casing such that the stator disc is parallel to the rotor disc and has an opening such that the shaft can pass through the stator disc,
  (e) optionally at least one running wheel attached to the shaft and containing openings such that when the shaft is rotating the running wheel provides a pumping effect to the reaction mixture passing through the mixer,
  (f) at least one inlet through the casing for introducing a phosgene solution axially to the shaft and against the rotor disc,
  (g) at least one inlet through the casing for introducing a mono- and/or polyamine solution or suspension against the rotor disc at a point which is radially outward from inlet (f),
by introducing the phosgene solution and the amine solution or suspension through inlets (f) and (g) while rotating the shaft, further reacting the reaction mixture at an elevated temperature downstream of the mixer and finally purifying the resultant isocyanate to form the mono- and/or polyisocyanate.

DETAILED DESCRIPTION OF THE INVENTION

Figure 1:
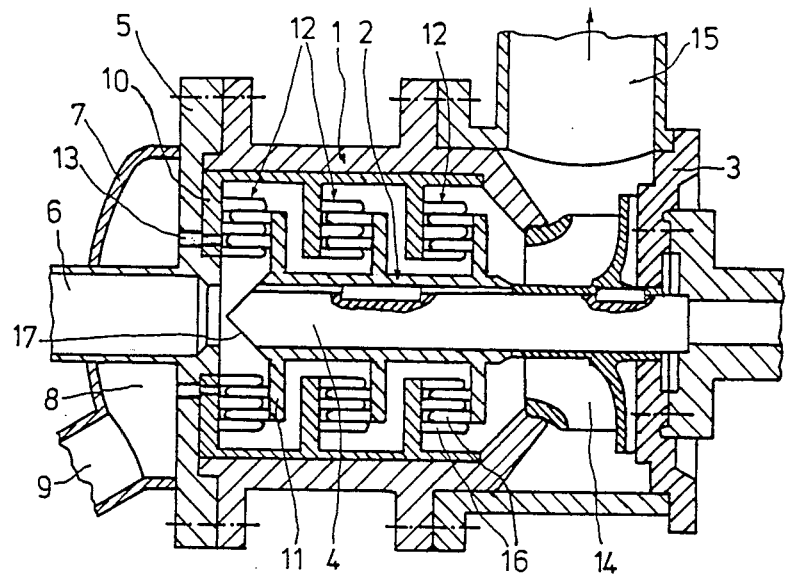

The mixer used in accordance with the present invention is the subject of copending application, Ser. No. 190,580.

Because the phosgene solution is led axially against the rotor disc, it streams radially outward and is admixed with the sprayed amine solution or suspension. Very good mixing results with a narrow residence time spectrum. Because of this, the danger of the formation of clumps and caking is minimized. By altering the shape of the rotor discs and stator discs, their distance from each other, the distance from the rotor disc to the casing or the distance from the stator disc to the shaft, the person skilled in the art can influence the flow conditions and thereby reduce back-mixing.

The amine present in solution or in suspension is preferably sprayed at several points surrounding the stream of the phosgene solution, e.g. around the face of the rotor disc. Of course, the nozzles are best arranged at the same angle, e.g. 90°, because this provides the best mixing conditions.

According to a further special embodiment of the new process, both substances are led through several stator disc/rotor disc units with continued mixing and conversion.

This variant is especially useful when high throughput rates are demanded, so that intensive phosgenation takes place. In particular, the front wall of the mixer, through which the substances are supplied, can be used simultaneously as the first stator disc.

To further improve mixing, the rotor discs and/or stator discs are preferably provided with stirring elements such as attached pins or concentric rings, or the discs are provided with holes or cut-away sections. All types of modifications, which are manufacturable in principle from a disc by means of holes, sections and/or attachments, are included within the scope of the invention.

For a narrow residence time spectrum, it is additionally preferred that the reaction mixture is transported through or away from the mixer by means of at least one running wheel. Such running wheels are generally arranged on the same shaft as the rotor disc and contain several openings which extend through the wheel. An additional stator is preferably provided before each running wheel to force the product through the openings in the running wheel. As the shaft rotates, the running wheel provides a pumping action to the reaction mixture to propel it through or away from the mixer. The rotor is driven with a rotation number between about 200 and 10,000 $min^{-1}$, preferably between about 1000 and 8000 $min^{-1}$.

Because phosgene is toxic, the mixer must be hermetically sealed. A magnetic coupling provided with a split tube is preferably provided to drive the mixer shaft.

The process is suitable for the phosgenation of any primary mono- and/or polyamine, especially for the production of the mono- and/or polyisocyanates useful in polyurethane chemistry. Starting materials for the process according to the invention are about 3 to 95% by weight, preferably about 20 to 75% by weight phosgene solutions in suitable solvents and about 5 to 95% by weight, preferably about 5 to 50% by weight solutions or suspensions of mono- and/or polyamines in suitable solvents. Amines suitable for the new process include primary mono- and/or polyamines such as methylamine, ethylamine, butylamine, stearylamine, phenylamine, p-tolylamine, 1,4-diaminobutane, 1,6-diaminohexane, 1,8-diaminooctane, 1,4-diaminobenzene, 2,4-diaminotoluene, 2,6-diaminotoluene, mixtures of the last-named isomers, 2,2'-diaminodiphenylmethane, 2,4'-diaminodiphenylmethane, 4,4'-diaminodiphenylmethane, mixtures of the three last-named isomers, alkyl-substituted diamines of the diphenylmethane series such as e.g. 3,4'-diamino-4-methyldiphenylmethane, polyamine mixtures of the diphenylmethane series as obtained in known manner by the aniline/formaldehyde condensation, p-xylylenediamine, perhydrated 2,4- and/or 2,6-diaminotoluene, 2,2-, 2,4- and/or 4,4-diaminodicyclohexylmethane, 1-amino-3,3,5-trimethyl-5-aminomethylcyclohexane (isophorone diamine or IPDA), lysine ethylester, lysine aminoethylester, 1,6,11-triaminoundecane or 1,5-naphthylenediamine.

Suitable solvents for the production of the phosgene and amine solutions include solvents that are inert under the reaction conditions such as chlorobenzene, o-dichlorobenezene, toluene, xylene, methylenedichloride, perchloroethylene, trichlorofluoromethane or butylacetate. Preferably chlorobenzene or o-dichlorobenzene are used. Any mixtures of the solvent given as examples can of course also be used. The use of the same solvent or mixtures of solvents for the amine components and the phosgene is effective, although this is not absolutely necessary.

The concentrations and relative proportions of amine and phosgene solutions can be varied within wide limits, provided that the quantity of phosgene must certainly be sufficient for the reaction. Therefore, the quantity of phosgene must be calculated so that at least 1 mole of phosgene is present per mole of primary amino groups. An equivalent ratio of phosgene to primary amino groups of about 2:1 to 30:1, preferably about 2:1 to 5:1 is effective. The temperature of the phosgene feed solution is about −25° to 25° C., while that of the amine solution is about 20° to 100° C. The phosgenation products after passing through the mixer can be conveyed into a downstream hot phosgenation stage, where (if necessary supplied by further phosgene), the conversion into the desired isocyanate is completed. Because of the very fine division of the phosgenation product, leaving the mixer, the reaction is completed in a shorter period and with fewer side-reactions than in other known processes.

The hot phosgenation stage downstream from the phosgenation process of the present invention can be any prior art process and is not critical to the phosgenation process of the invention. The hot phosgenation can be conducted continuously or discontinuously with or without the addition of additional phosgene under increased pressure, slightly increased pressure or normal pressure.

Preferably, the hot phosgenation is carried out continuously in towers under normal pressure or very slightly increased pressure up to roughly 1.5 atmospheres. It is particularly advantageous to allow the phosgenation mixture leaving the mixing device to enter continuously from above or below into a heatable tower and to complete the reaction by adding heat. Several towers can also be arranged in series or combinations of boilers and towers can be used, if a preset temperature profile is to be maintained for the optimizing reaction in the hot phosgenation stage.

The isocyanate solution thus obtained can be worked up to the isocyanate by distillation and/or crystallization in known manner. An advantage of the process of the present invention is that a particularly small content of undesired side products is present and, thus, particularly high yields of the pure isocyanates are obtained. In the unpurified isocyanate mixtures, the low content of side products is recognizable from the high content of free isocyanate groups.

In the drawing, a mixer is represented schematically in sectional views of embodiments, which are suitable for carrying out the first process step.

Figure 2:
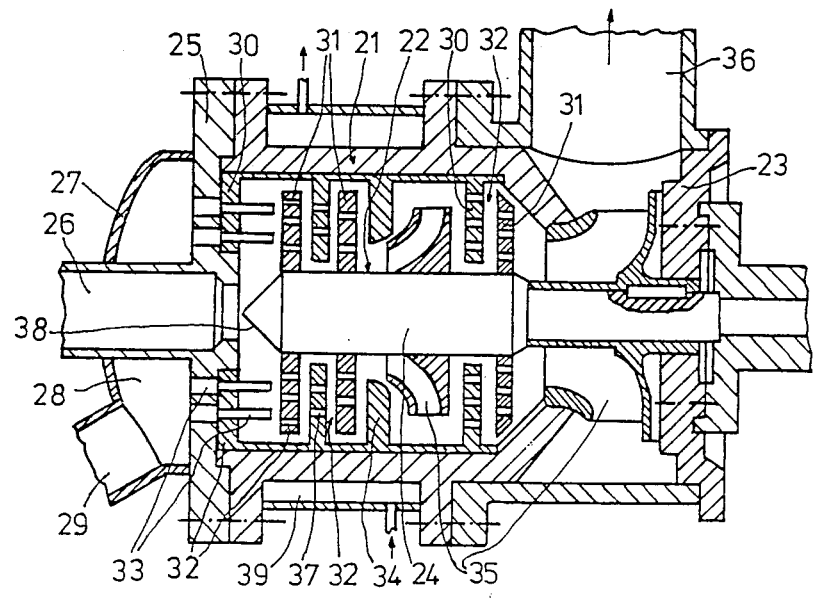

FIG. 1 shows a mixer with stirring elements on the stator discs and on the rotor discs and FIG. 2 shows a mixer with two running wheels.

In FIG. 1, the mixer is made up of a casing 1 and a rotor 2. The shaft 4 of rotor 2 extends into wall 3 and is hermetically sealed to the outside. The drive takes place across a magnetic coupling (not represented). Front wall 5 is provided with a supply connecting piece or inlet 6 for conveying the phosgene solution. A hood 7 is arranged on the outside of front wall 5, so that a chamber 8 is formed. A feeder 9 for an amine solution joins into chamber 8. A stator disc 10 is arranged at the inner side of front wall 5, which, together with a first rotor disc 11 arranged on the shaft 4 forms a first unit 12. Nozzles 13 project from chamber 8 through front wall 5 and stator disc 10 and join directly in front of rotor disc 11. The casing 1 encloses two more, similarly constructed stator disc/rotor disc units 12, which are arranged in series. The casing narrows after the last unit 12 to a running wheel 14. A connecting piece 15 is provided in proximity to running wheel 14 region from which a pipe (not represented) leads to the subsequent hot phosgenation stage. Both stator discs 10 and rotor discs 11 are provided with rods as stirring elements 16, which are arranged in the shape of concentric, meshing collars. The front surface 17 of shaft 4 tapers towards inlet 6.

In FIG. 2, the mixer is based on a casing 21 and a rotor 22. The shaft 24 of the rotor 22 extends into wall 23 and is hermetically sealed off from the outside. The drive takes place across a magnetic coupling (not represented). Front wall 25 is provided axially to shaft 24 with a feeder connecting piece or inlet 26 for a phosgene solution. A hood 27 is arranged on the outside of front wall 25, forming a chamber 28. A feeder 29 for an amine suspension joins into chamber 28. A stator disc 30 is arranged on the inner side of front wall 25, forming a unit 32 with a first rotor disc 31 arranged on shaft 24. Feed nozzles project out of chamber 28 through front wall 25 and stator disc 30 and lead directly in front of rotor disc 31. Two more stator disc/rotor disc units 32 are provided, wherein an additional stator disc 34 and a first running wheel 35 are provided between the second and third unit 32. Casing 21 tapers behind the third unit 32 up to a second running wheel 35. A connecting piece 36 leads out from casing 21. An unrepresented connecting main leads to a downstream hot phosgenation stage. The first stator disc 30 serves for the admittance of nozzles 33, while the further stator discs 30 and rotor discs 31 have slits as stirring elements 37. The front surface 38 of shaft 24 is tapered towards inlet 26 is tapered. The casing 21 is provided with a tempering jacket 39.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a mono- and/or polyisocyanate by the phosgenation of a mono- and/or polyamine in a mixer which comprises
   (a) a casing having at least two inlets and at least one outlet,
   (b) a rotatable shaft extending through said casing,
   (c) at least one rotor disc attached to said shaft such that said rotor disc is perpendicular to said shaft,
   (d) at least one stator disc attached to said casing such that said stator disc is parallel to said rotor disc and has an opening such that said shaft can pass through said stator disc,
   (e) optionally at least one running wheel attached to said shaft and containing openings such that when the shaft is rotating said running wheel provides a pumping effect to the reaction mixture passing through said mixer,
   (f) at least one inlet through said casing for introducing a phosgene solution axially to said shaft and against said rotor disc,
   (g) at least one inlet through said casing for introducing an amine solution or suspension against said rotor disc at a point which is radially outward from inlet (f), which comprises introducing said phosgene solution and said amine solution or suspension through inlets (f) and (g) while rotating said shaft, further reacting said reaction mixture at an elevated temperature downstream of said mixer and finally purifying the resultant isocyanate to form the mono- and/or polyisocyanate.

2. The process of claim 1 wherein said mixer comprises more than one inlet for introducing a second substance.

3. The process of claim 1 wherein said mixer comprises more than one rotor disc and more than one stator disc.

4. The process of claim 2 wherein said mixer comprises more than one rotor disc and more than one stator disc.

5. A process for the production of a mono- and/or polyisocyanate by the phosgenation of a mono- and/or polyamine in a mixer which comprises
   (a) a casing having at least two inlets and at least one outlet,
   (b) a rotatable shaft extending through said casing,
   (c) at least one rotor disc attached to said shaft such that said rotor disc is perpendicular to said shaft,
   (d) at least one stator disc attached to said casing such that said stator disc is parallel to said rotor disc and has an opening such that said shaft can pass through said stator disc,
   (e) at least one running wheel attached to said shaft and containing openings such that when the shaft is rotating said running wheel provides a pumping effect to the reaction mixture passing through said mixer,
   (f) at least one inlet through said casing for introducing a phosgene solution axially to said shaft and against said rotor disc,
   (g) at least one inlet through said casing for introducing an amine solution or suspension against said rotor disc at a point which is radially outward from inlet (f), which comprises introducing said phosgene solution and said amine solution or suspension through inlets (f) and (g) while rotating said shaft, further reacting said reaction mixture at an elevated temperature downstream of said mixer and finally purifying the resultant isocyanate to form the mono- and/or polyisocyanate.

6. The process of claim 5 wherein said mixer comprises more than one inlet for introducing a second substance.

7. The process of claim 5 wherein said mixer comprises more than one rotor disc and more than one stator disc.

8. The process of claim 6 wherein said mixer comprises more than one rotor disc and more than one stator disc.

* * * * *